Figure 1:
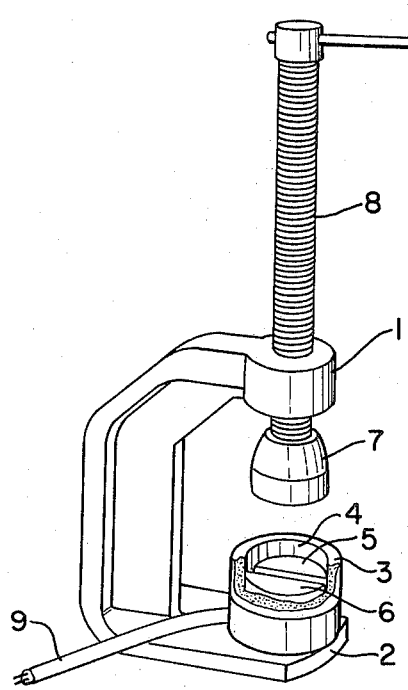

United States Patent [19]

Steele

[11] 4,392,127
[45] Jul. 5, 1983

[54] MOISTURE METERS OF A TYPE ESPECIALLY SUITABLE FOR ESTIMATING THE MOISTURE CONTENT OF ORGANIC MATERIALS

[76] Inventor: Derek E. Steele, 61A Baden Ter., O'Sullivan Beach, South Australia, Australia, 5166

[21] Appl. No.: 224,540

[22] PCT Filed: Apr. 10, 1980

[86] PCT No.: PCT/AU80/00002
§ 371 Date: Dec. 10, 1980
§ 102(e) Date: Dec. 10, 1980

[87] PCT Pub. No.: WO80/02199
PCT Pub. Date: Oct. 16, 1980

[30] Foreign Application Priority Data

Apr. 10, 1979 [AU] Australia .................. PD8367

[51] Int. Cl.³ .................. G08B 21/00; G01N 27/04
[52] U.S. Cl. .................. 340/604; 324/65 R
[58] Field of Search .................. 340/604, 603, 602; 324/65 R, 65 CP

[56] References Cited

U.S. PATENT DOCUMENTS

| | | | |
|---|---|---|---|
| 2,043,241 | 6/1936 | Ever | 340/604 |
| 2,582,629 | 1/1952 | Hilton | 324/65 R |
| 2,673,327 | 3/1954 | Morelock | 324/65 R |
| 3,005,153 | 10/1961 | Berkley et al. | 324/65 CP |
| 3,331,020 | 7/1967 | Farenkoff | 324/65 R |
| 3,490,040 | 1/1970 | Roberts | 324/65 R |
| 3,961,247 | 6/1976 | Toki | 324/65 R |
| 4,122,389 | 10/1978 | Haagen | 340/604 |
| 4,259,633 | 3/1981 | Rosenau | 324/65 R |

Primary Examiner—Gerald L. Brigance
Attorney, Agent, or Firm—Oldham, Oldham, Hudak & Weber Co.

[57] ABSTRACT

A grain moisture testing apparatus which can be used for testing of moisture content of other organic materials includes means to hold and crush the material against conductance measuring electrodes. These electrodes form one element of a voltage divider, the other element of which is formed by a resistor which is selectively adjustable among several distinct values. The resistance between the two electrodes, and thus the moisture content of the material proportional thereto, is determined by applying a constant voltage across the divider and sensing the voltage occuring across the electrodes. The voltage sensor is designed as a threshold switch which gives a simple Pass/Fail indication of acceptable moisture level. The apparatus also includes voltage supply testing means and circuit temperature testing and compensation means to assure the validity of the test.

5 Claims, 4 Drawing Figures

MOISTURE METERS OF A TYPE ESPECIALLY SUITABLE FOR ESTIMATING THE MOISTURE CONTENT OF ORGANIC MATERIALS

This invention relates to grain moisture testing apparatus.

In some industries and especially in wheat and barley growing industries it can be essential for the long term storage of grain to know the moisture content of this grain.

Farmers may not have their crop accepted at a silo unless it is below a given moisture level and it can be quite essential that prior to harvesting grain, the farmer knows within adequate limits the moisture content of the grain so that he can be assured that the product in the silo will not unduly promote mould growth.

Indeed, if the farmer is mistaken with moisture level of his grain he may be required to provide costly additional drying prior to the acceptance of this material in the silo.

It is known to measure moisture level or organic material by crushing the material and then measuring conductance across a specified thickness of the crushed material.

This conductance is then compared to known standard conductances of similar materials for known moisture contents and related to the temperature at which the test is taken and a reasonably accurate estimate of the moisture content can then be obtained.

In a most popular instrument at the present time, there are provided means by which the conductance of the material can be obtained by using the well known principles of the wheatstone bridge and by using conventional techniques of firstly zeroing the readings and then obtaining a null point reading the conductance of the material can be obtained which can then be compared by tables with comparable conductances of known samples in relation to temperature and an accurate estimate of the moisture content for a standard temperature can then be assessed.

A first problem with this arrangement is the cost of the equipment necessary to achieve firstly an accurate and secondly a reliable measure of conductance in the circumstances.

To explain this further, one of the big difficulties is that the conductance of the sample will vary considerably from some thousands of megohms down to a few kilohms and especially at the higher ohmic readings, difficulties are experienced firstly with providing accurate and temperature stable ohmic references and secondly, because of the small currents involved in obtaining an accurate null reading, the use of very sensitive field effect transistors while very useful does make the instrument very prone to electrostatic voltages interfering with an accurate reading.

Also perhaps most importantly, the instrument while very suitable for those who are fully trained in the use of the instrument is not clearly useful for the normal person most likely to require to use the machine such as a farmer and herein perhaps lies the biggest difficulty. One generally must understand the principles of zeroing and finding the null reading and understanding the terminology and therefore such complicated steps require firstly that the person have some understanding and training and they do promote the high possibility of errors in the use of the machine.

There is a further difficulty in that inherently the system requires manually variable resistors and as the machines are used in situations where atmospheric conditions can be poor, long term maintenance of such a machine becomes a difficulty and reliability of the readings becomes less sure after a period of usage.

A further problem recalling that for accurate measurement, very high quality and therefore inherently expensive machines have hitherto been required but even with such previous macines, because in measuring moisture content, very high variations in resistances are necessary and it is inherently necessary to use in such machines as have hitherto been made, potentiometers generally known as having logarithmic variation in resistance characteristics.

Unfortunately, in practice such resistors as are commonly offered for purchase and use in electronic equipment are only an approximation of a logarithmic variation in resistance values, for instance typically if a wire-wound potentiometer is used, the wire varies its resistance by having sections of the same resistance per unit length over a set distance.

This means that the variation in resistance varies in short steps which over the full variation will approximate a logarithmic variation in resistance but where accurate measurement is necessary and repeatability of results, this problem makes it extremely difficult.

An aspect of this invention resulted from the realization that in practical applications in agriculture most farmers only need to know that the moisture reading is within selected limits.

Further, it was appreciated from an electronic point of view that it is considerably more economic to provide a reference by way of a regulated voltage reference with calibrated resistances over a significant range.

The problem of course still remains that there is a variation in interpretation with temperature. It was further appreciated then that a range of values could be proposed for a given standard temperature and that it would not be difficult for a farmer to make a direct comparison on a table in relation to the actual moisture reading for a given temperature.

There is one further aspect namely that the moisture content as compared to the conductance varies in accord with the different type of organic material being measured. Again it has been realized that most growers concentrate on one or perhaps at most two types of grain and that a machine can still be extremely useful if in fact calibrated only for one type of grain with if necessary comparison tables.

The assumptions from a practical and marketing sense provide significant advantages from an electronic point of view and with further development unique circuit concepts have been devised for this application which avoid some of the hitherto experienced electronic problems with apparatus hitherto used as well as some of the practical problems such as the use of variable resistances necessary in gaining measurements.

Finally and perhaps most importantly, significant price reductions are possible without losing any of the significant advantage in practical terms that has been considered apparently essential hitherto.

According to one form of this invention this can be said to reside in apparatus for the testing of moisture content of organic materials such as grain to be operated in conjunction with means to crush organic materials and hold electrodes with contact faces a selected distance apart holding there between such crushed organic materials the apparatus being characterised according to this invention in that the apparatus includes indicator means arranged to indicate at least a substantially digital answer that is, a true or false status indicator, and switch means to select a moisture level whereby to connect such indicator means to the electrodes so as to give an indication of whether the material on the test is above or below a selected moisture level.

Perhaps in another form the invention can be said to reside in a grain moisture testing apparatus of a type including means to hold grain under crushing compression within a cell including two electrodes each with a contact face to be in contact with the cell with crushed grain, and conductance testing means connected to the electrodes, the apparatus being characterised according to this invention in that the conductance testing means include a source of substantially constant voltage, a plurality of separately selectable voltage dividers including as one of each of the elements of any of a selected voltage divider, the resistance between the said two electrodes within the cell, a predetermined voltage level detection means, an output of the selected voltage divider being connected to the voltage level detection means, and indicator means connected to the said voltage level detection means and arranged whereby to indicate upon a voltage input into the voltage level detection means whether such voltage is above or below the said predetermined voltage level.

In a practical situation, it has been found that if the output of the selected voltage divider comprising a voltage is equal to or very close to the predetermined voltage at which the voltage level detection means will activate the indicators, then there can be to some extent a slight overlap of the yes and no answer, in other words in the event lights shine when it is yes or no, a partial lighting will be possible indicating close coincidence of the input voltage with respect to the threshold voltage level of the detector.

Preferably, the threshold level detector comprises a pair of transistors arranged as a darlington pair and it has been found that there is a very well defined and stable knee voltage with respect to conventional transistors used in this arrangement so that a voltage of typically one volt will act to critically switch on and cause a significant output from the darlington pair which can be used then to effect a turn-off or turn-on of some indicator means.

While temperature can vary the switch-on voltage, it has been found in practice that the voltage does not vary significantly with temperature and with some balancing of temperature compensation elements, temperature so far as components of the type used can be used in significantly varying temperature situations without being unduly affected with subsequent loss of accuracy.

According to a further concept there are provided selected resistances coupled by switching means so as to be comparable with the resistance of the sample under test and the circuit being arranged so as to provide a voltage the level of which depends upon the said comparison of the two resistances and voltage threshold detection means responsive to the level of said voltage to give the indicator output.

By having a selected resistor in series with the resistance of the sample and subjecting both of these to a regulated voltage, a voltage can be generated the level of which can be easily used to trigger a selective voltage threshold detection means dependent upon the comparison ratio but by using such an arrangement, the comparison resistances need not be of a significantly high order or at least can be some magnitudes less than the compared resistance without losing too much accuracy as will be seen in the preferred embodiment.

The resultant voltage output in itself can be amplified or it can be fed onto a trigger device sensitive to a selected threshold value of voltage but in any event an output can be achieved which can be fed onto a resistor divider chain from which an active true reading can be read or an active false reading can be read.

Figure 2:
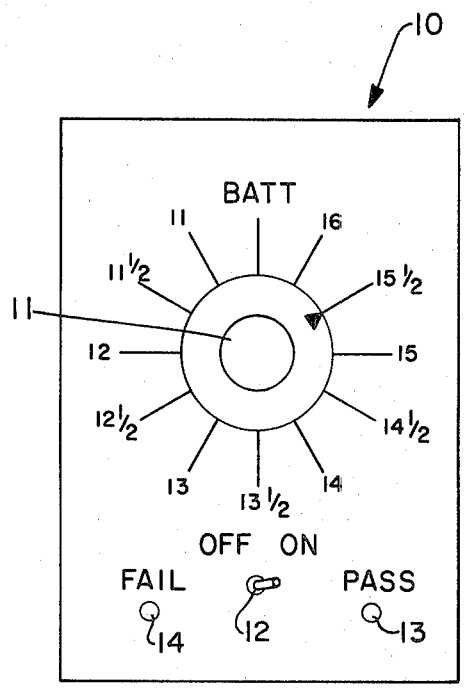
Figure 4:
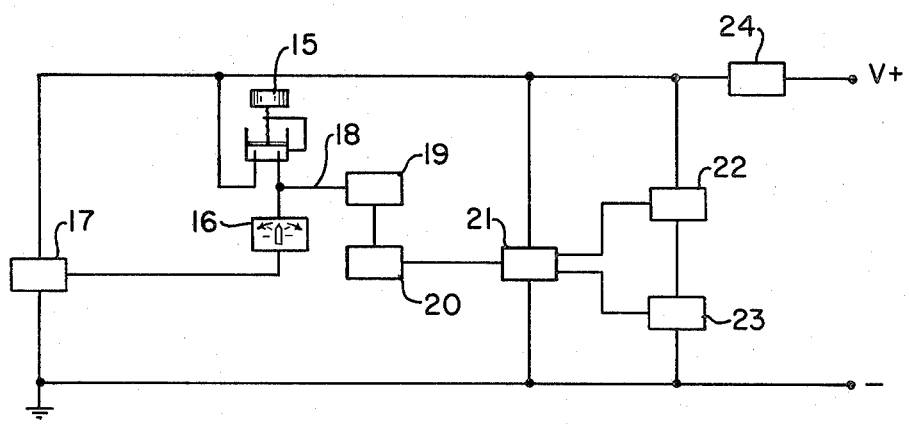
Figure 3:
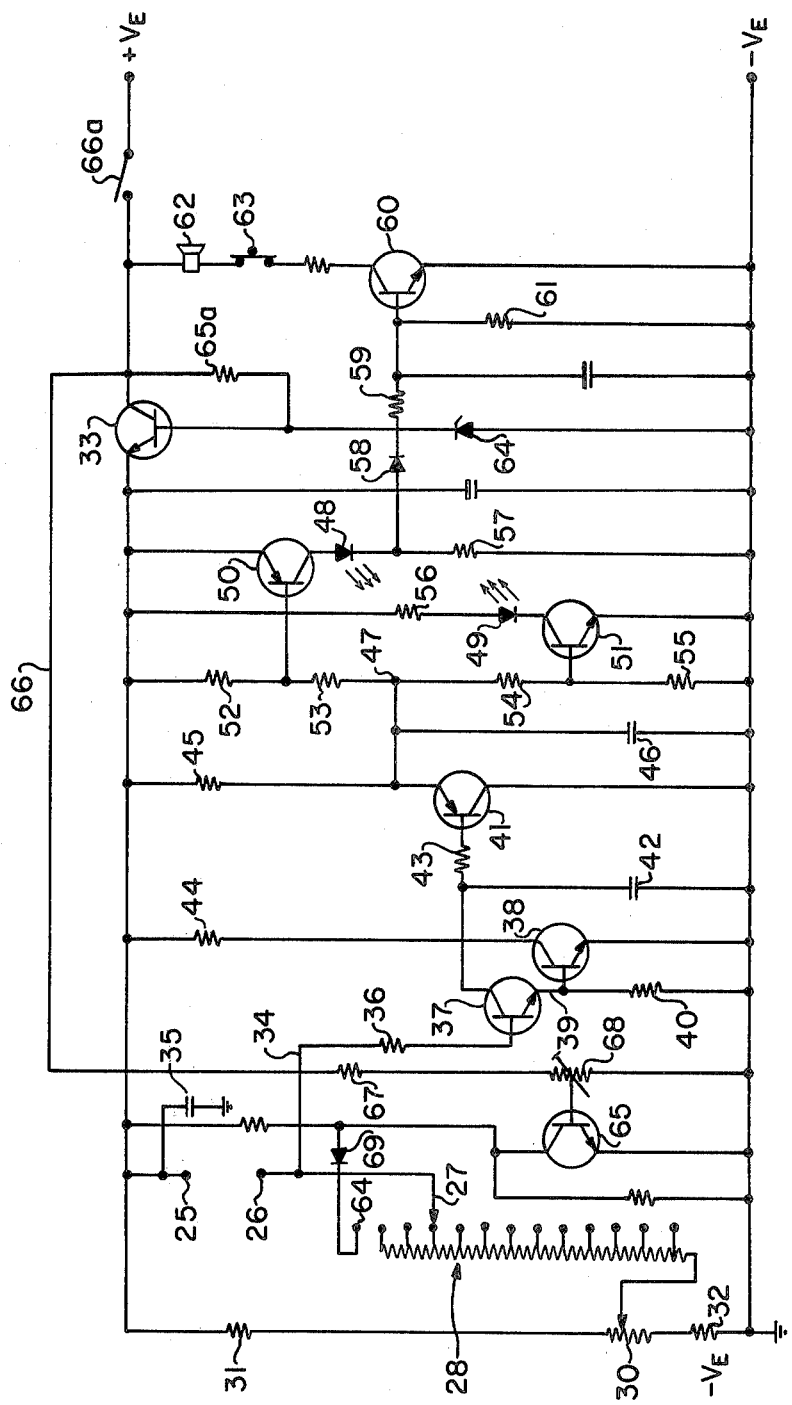

For a better understanding of the invention reference shall now be made to a preferred embodiment which shall be described with the assistance of drawings attached hereto and in which:

FIG. 1 is a perspective view of a device for holding grain under crushing compression within a cell and including two lower electrodes each with a contact face to be in contact within the cell with crushed grain, FIG. 2 illustrates the control panel of a conductance testing means according to the preferred embodiment showing the pass and fail indicators comprising in each case light emitting diodes (L.E.D.'s) of different colour and the means for selecting one of a number of voltage dividers which will give a measure of the conductance of the crushed grain within the compression cell, there also being shown a battery test position and an all up on or off switch, FIG. 3 is a circuit diagram showing the circuit elements and arrangement for the preferred embodiment comprising the conductance testing means, and FIG. 4 is a schematic layout showing some of the functional elements comprising the most basic form of the invention incorporated within the embodiment.

Referring to the drawings in detail, and referring to the compression cell and compression means shown in FIG. 1 this includes a clamp 1 which has supported on an anvil portion 2 an annular enclosing ring 3 forming a cell 4 into which grain or other organic material to be measured can be placed.

The floor of the cell thus formed comprises two electrodes 5 and 6 each having a contact face being shown of generally semi-circular shape and comprising the uppermost face of the electrode in each case so as to provide a contact area against which the grain shall be crushed.

The crushing is achieved by piston 7 being screwed by means of screw 8 into a crushing situation so as to push the grain until fully crushed against the electrodes 5 and 6.

The electrodes 5 and 6 are coupled in electrical manner by means of cable 9 to conductance testing means as shown in the other figures as 10.

Referring now to FIG. 2 this shown the conductance measuring apparatus 10 including a selector switch 11 which selects a number of test positions which when the switch 12 is in the on position there will be given an indication by the lighting either of a pass light 13 or the lighting of a fail light 14.

A fail indication is arranged on the basis that the conductance across the electrodes of the compression cell at a selected temperature (25° C. being the temperature normally selected) is higher than grain of the selected type would exhibit if having a moisture content as indicated on the selector switch dial plate.

In other words, with standard conditions of temperature and of grain type, a fail will indicate greater moisture content of the sample.

Likewise a pass will indicate a lower moisture content of the sample.

It will be seen that there is also a selector position for the switch with the abbreviation BATT which stands for battery check and when the selector switch is in this position, it is so arranged to also operate the fail or pass lights but in this case it indicates whether the battery condition is adequate namely is the battery delivering adequate voltage for the tests to be valid or within tolerance range.

Referring now to FIG. 4 this comprises a number of functional elements shown in very schematic form by which the arrangement of the embodiment can be perhaps more easily visually ascertained.

Accordingly the means to hold grain under crushing compression within a cell 15 is connected in series with a plurality of voltage dividers which can be selected this being shown at 16 and there being calibration resistors at 17 to provide calibration settings for the resistant dividers in the block 16.

The output from the voltage dividers in combination with the compression cell 15 is shown at 18 and this is fed to a threshold voltage detector 19 the output of which is fed into an amplifier 20 the output of which is fed into a pass or fail selector 21.

The pass or fail selector selectively drives either the fail indicator 22 or the pass indicator 23.

The voltage providing the powering of the various elements including the voltage divider is regulated by voltage regulator device 24.

This then describes the fundamental elements but for a fuller understanding of how this can be used in practice together with additional features especially some means to determine that the voltage supply is adequate at any time reference shall now be made to the much fuller disclosure as set out in the circuit drawing of FIG. 3.

The compression cell is to be connected to connections 25 and 26 which are connected to switching element 27 by which one or more of the resistances in the series of resistances 28 can be selected.

The series of resistances 28 are connected by means of the variable resistance 30 and in series resistances 31 and 32 so as to provide a calibration position so that with a selected voltage coming from regulator means 33 the output voltage on line 34 will correspond at a selected temperature which is conventionally taken as 25° C. to a moisture reading value as shown on the indicator plate adjacent the selector switch.

It is to be noted that resistor 32 is a thermistor with a negative coefficient so providing temperature compensation to the calibration settings.

Typically the resistor 31 is a one K resistor the variable resistor 30 is 500 ohms and the thermistor having the negative coefficient is 33 ohms.

These are given as illustrative of typical values that will be useful.

Capacitor 35 is a decoupling capacitor to ground unwanted AC signals that might be induced in the network.

The voltage resulting from the divider network the elements of which are selected by selector switch 27 is fed through resistor 36 onto the base of the first of two transistors 37 and 38 which are connected as a darlington pair the connecting rail 39 being tied to earth through a 10 meg resistor 40.

The darlington pair comprises two npn transistors of a type such as BC549C.

It has been discovered that such transistors especially coupled in the darlington arrangement exhibit very sharp threshold voltage sensitivity.

In the illustrated arrangement with the described transistors a threshold detection level of one volt results in very significant change in output with minimal changes of input voltage.

This so called knee characteristic is taken full advantage of in this arrangement and used to provide a very sharp threshold voltage detector which has only modest change in response by reason of temperature variation.

The output of the darlington pair is fed onto the base of a pnp transistor 41 which is of a type such as BC559 the signal being decoupled through condenser 42 and fed through very high resistance 43 which is of a value 470k there also being a loading resistor 44 also being of the value 470k.

The transistor 41 acts as an amplifier the output of which is fed through load resistor 45 which is decoupled by condenser 46 the output of which is fed into the resistance divider arrangement 47.

There are two light emitting diodes one of these being 48 which is a fail indicator and the other 49 which is a pass indicator in each case being fed by a transistor in the case of the fail indicator the pnp transistor 50 and in the case of the pass transistor the npn transistor 51.

The bases of each of the respective transistors 50 and 51 are fed from a voltage divider arrangement comprising the four resistances 52, 53, 54 and 55 each of these being of the value of 100k ohms.

The light emitting diodes in each case are also additionally loaded with resistors 56 and 57 in each case these being 470 ohms in value.

A signal from the fail load is taken by way of diode 58 through resistor 59 and fed onto npn transistor 60 which is biased by resistor 61 this controlling the drive or otherwise of a piezo-electric acoustic alarm 62.

This part of the circuit can be operated selectively by operation of push button 63.

There is a voltage regulator 33 the base of which is controlled by its connection through zener diode 64 which in the preferred instance as shown comprises an 8.2 voltage zener based on the nominal supply voltage from source of 9 volts.

An additional feature of the circuit shown is means by which the status of the nominal voltage can be checked that is when this is supplied from a battery it can be determined as to whether this is adequate for valid readings.

This operates by selector switch 27 being connected to contact 64 which couples the output of npn transistor 65 onto the base via line 34 of the darlington pair of transistors 37 and 38.

The switching on or otherwise of transistor 65 is achieved by using a reference connection by way of line 66 which proceeds through resistance 67 and variable resistance 68 to provide a calibrating reference for switch on or otherwise of this transistor 65.

The setting is set so that when the voltage of the input is below a selected level, this will effectively switch the transistor 65 off so that the voltage upon the transistor being switched on will raise the voltage fed into connection 64 through diode 69 which in turn operates through the darlington pair 37 and 38 and through the amplifier transistor 41 to effect a lighting of the fail light indicating the low voltage status of the battery.

This then describes in general terms the elements of the circuit which are generally important to its operation it being acknowledged that the elements are conventional elements and that their use as functional elements in some instances is generally according to conventional techniques which will be familiar very much so to those familiar with this art.

The operation of the circuit will be also fairly readily seen by those familiar with this art but nonetheless a description in simple terms of its function may assist in a further and better understanding of the invention.

Accordingly presuming a lower moisture level than the setting calls for effecting therefore a higher resistance between the electrodes 25 and 26 then this causes a lowering of the voltage 34 below the threshold level which will turn on the darlington pair 37 and 38 so that this will in turn effect a higher resistance in transistor 38 which in turn will raise the voltage significantly at the output of resistor 43 which in turn will turn off transistor 41.

The result of this will be to alter the bias levels on the respective transistors 50 and 51 so that 51 will conduct and 50 will not so that there is an effective indication by reason of current transferring through LED 49 showing a pass indication.

Conversely with a lower resistance between electrodes 25 and 26 this in turn will raise the voltage through output 34 into the darlington pair 37 and 38 which in turn will lower the voltage at the output of resistor 43 which in turn will cause transistor 41 to conduct and this will lower the voltage at 47 with the resultant altering of the bias levels of the respective transistors 50 and 51 so that 51 will not conduct and 50 will hence lighting light emitting diode 48 which is indicating a fail condition.

The output from the transistor 50 is taken and amplified through transistor 60 so that if there is any significant current flowing in this output lead then this can be detected and perhaps amplified by the audio indicator 62.

Incidentally, there is a stabilising resistor 65a of 5.6k ohms across the regulator transistor 33.

There is an off/on switch 66a.

This then describes the embodiment as applied to a specific case and from which it will be seen that circuit elements especially relating to voltage division need not be critical for good moisture level determination and in practice the circuit as described has shown outstanding results and reliability and it has been able to be manufactured from standard components while exhibiting very high degrees of repeatability of readings and can be manufactured at very economic prices.

A feature of the embodiment relates to the way in which the separately selectable voltage dividers are not supplied directly with line volts.

Instead, while the cell electrodes and the selected resistances to be connected to this are fed from the positive line, the earth end of the divider is connected to the pre-set resistor which forms with the additional resistances in that line a chain of resistors acting as a voltage divider which together have relatively low resistances.

One of the problems that has been experienced is that with grain which is relatively dry for instance having moisture content of perhaps 10% moisture or less, the actual conductance is very low, that is the resistance is very high and indeed the resistance is so high that it is very difficult to obtain standard resistances of reliable performance characteristics and having these economically available which can act in series with the electrodes in the cell without making the ratio of division too high. The problem with this is that the tolerance of the resistors becomes too critical and this is an undesirable characteristic.

By providing therefore that the negative line reference comes from a relatively low resistance divider fed from line volts to earth return the actual voltage drop required across the selected resistors is then able to be much less than would hitherto have been necessary if the negative end of the divider had been referred to earth.

This in turn means that the actual values of resistance can now be considerably less than has hitherto been necessary so that it becomes economically reasonable to use standard howbeit high value resistances in the selected divider chains. The practical result of this is that relatively low values of moisture content can now be economically ascertained with apparatus of this type whereas previously this was considered not to be possible in the sense of using relatively economic apparatus.

Whereas throughout this specification reference has been made to the application of this apparatus to the testing of grain, it is to be emphasized that this is illustrative of the application but clearly a number of organic materials can be also used provided that the apparatus is appropriately calibrated. The reference therefore to "grain" is illustrative and not intended to be a limiting reference in respect to the application of this apparatus or invention.

I claim:

1. A grain moisture feeding apparatus, comprising: means to hold grain under crushing compression within a cell, said cell containing two electrodes each with a contact face to be in contact within the cell with crushed grain and conductance testing means connected to the electrodes, said testing means including a source of substantially constant voltage, a voltage divider connected across said voltage source, said voltage divider containing two elements, one of said elements being the resistance between the two electrodes within the cell and the other element including a resistor which is selectively adjustable among several distinct values a predetermined voltage level detection means, the junction between the two elements of said voltage divider being connected to said voltage detection means, and indicator means connected to the said voltage level detection means and arranged to indicate whether the voltage connected across the voltage level detection means is above or below the said predetermined voltage level.

2. A grain moisture testing apparatus as in claim 1 wherein the voltage level detection means comprises transistors connected as a darlington pair with the predetermined voltage level being the switching value of the darlington pair.

3. A grain moisture testing apparatus as recited in claim 2 wherein there are included means for testing and indicating if the source of substantially constant voltage falls below a selected voltage level.

4. A grain moisture testing apparatus according to claim 2 wherein said other element of said voltage divider also includes a variable calibrating resistor and a resistance having a negative coefficient with respect to temperature.

5. A grain moisture testing apparatus according to claim 1 in which the indicator means comprises two light emitting diodes, a first light emitting diode arranged to be lighted when the voltage across the voltage level detection means is higher than the predetermined voltage level and a second light emitting diode is lighted when the voltage across the voltage level detection means is below the said predetermined voltage level.

* * * * *